(12) United States Patent
Kumar et al.

(10) Patent No.: US 11,106,934 B2
(45) Date of Patent: Aug. 31, 2021

(54) AUTOMATIC VISUAL DISPLAY OVERLAYS OF CONTEXTUALLY RELATED DATA FROM MULTIPLE APPLICATIONS

(71) Applicant: INNOVACCER INC., San Francisco, CA (US)

(72) Inventors: Krishna Kumar, Navi Mumbai (IN); Rijul Zalpuri, Noida (IN); Mudit Saxena, Sikar (IN); Ankit Maheshwari, Noida (IN)

(73) Assignee: INNOVACCER INC., San Francisco, CA (US)

( * ) Notice: Subject to any disclaimer, the term of this patent is extended or adjusted under 35 U.S.C. 154(b) by 0 days.

(21) Appl. No.: 16/568,830

(22) Filed: Sep. 12, 2019

(65) Prior Publication Data

US 2020/0257920 A1    Aug. 13, 2020

(30) Foreign Application Priority Data

Feb. 11, 2019    (IN) .............................. 201921005335

(51) Int. Cl.
| | |
|---|---|
| *G06F 3/0481* | (2013.01) |
| *G06K 9/46* | (2006.01) |
| *G06T 1/00* | (2006.01) |
| *G16H 10/60* | (2018.01) |
| *G16H 30/40* | (2018.01) |
| *G06K 9/34* | (2006.01) |

(52) U.S. Cl.
CPC .......... *G06K 9/4609* (2013.01); *G06K 9/344* (2013.01); *G06T 1/0014* (2013.01); *G16H 10/60* (2018.01); *G16H 30/40* (2018.01); *G06K 2209/01* (2013.01)

(58) Field of Classification Search
CPC ...... G16H 30/40; G06T 1/0014; G06K 9/344; G06K 2209/01; G06F 3/0481
See application file for complete search history.

(56) References Cited

U.S. PATENT DOCUMENTS

| | | | |
|---|---|---|---|
| 6,373,507 B1 * | 4/2002 | Camara .................. | G06F 3/0481 345/902 |
| 6,408,294 B1 | 6/2002 | Getchius ........... | G06F 16/24534 |

(Continued)

OTHER PUBLICATIONS

U.S. Appl. No. 16/363,897, filed Mar. 25, 2019, Bhabesh et al.

(Continued)

*Primary Examiner* — Phenuel S Salomon
(74) *Attorney, Agent, or Firm* — Hayes Soloway P.C.

(57) ABSTRACT

Systems and methods for automatic visual display overlays of contextually related data from multiple applications are provided. The method includes: capturing an image of at least a portion of a graphical user interface (GUI) of a first application visually displayed on a computerized display device; identifying at least one primary contextual data point within the captured image; searching for at least one secondary data point in at least a second application, wherein the at least one secondary data point is contextually relevant to the primary contextual data point; fetching the at least one secondary data point from the second application; and visually displaying a panel on the computerized display device concurrently with at least a portion of the GUI of the first application, wherein the panel includes the at least one secondary data point.

18 Claims, 16 Drawing Sheets

(56) References Cited

U.S. PATENT DOCUMENTS

| | | | |
|---|---|---|---|
| 6,484,161 B1 | 11/2002 | Chipalkatti | G06Q 30/02 |
| 6,680,749 B1* | 1/2004 | Anderson | H04N 5/232 |
| | | | 348/231.99 |
| 7,551,783 B2* | 6/2009 | Johnson | G06K 9/00 |
| | | | 348/160 |
| 8,656,265 B1* | 2/2014 | Paulin | G06F 16/957 |
| | | | 715/205 |
| 8,849,693 B1 | 9/2014 | Koyfman | G06Q 30/02 |
| 9,727,591 B1 | 8/2017 | Sharma | G06F 16/215 |
| 10,147,504 B1 | 12/2018 | Stettin et al. | G16H 50/30 |
| 2003/0018633 A1 | 1/2003 | Horn | G06F 17/18 |
| 2004/0215629 A1 | 10/2004 | Dettinger | G06F 16/2452 |
| 2004/0215981 A1* | 10/2004 | Ricciardi | G06Q 50/24 |
| | | | 726/27 |
| 2007/0239724 A1 | 10/2007 | Ramer | G06F 16/951 |
| 2009/0244278 A1* | 10/2009 | Taneja | H04N 7/147 |
| | | | 348/143 |
| 2010/0121879 A1* | 5/2010 | Greenberg | G06F 16/248 |
| | | | 707/779 |
| 2010/0199169 A1* | 8/2010 | Gnech | G06F 16/972 |
| | | | 715/234 |
| 2010/0324936 A1* | 12/2010 | Vishnubhatla | G06Q 50/22 |
| | | | 705/3 |
| 2011/0099514 A1 | 4/2011 | Singhal et al. | G06F 3/048 |
| 2011/0153653 A1* | 6/2011 | King | G06F 16/5846 |
| | | | 707/769 |
| 2011/0238768 A1* | 9/2011 | Habets | G06F 19/321 |
| | | | 709/206 |
| 2012/0070090 A1* | 3/2012 | Chang | G06F 3/005 |
| | | | 382/218 |
| 2012/0317549 A1* | 12/2012 | Cunningham | G06F 11/3612 |
| | | | 717/128 |
| 2013/0111001 A1* | 5/2013 | Hamilton | H04L 41/04 |
| | | | 709/223 |
| 2013/0124499 A1* | 5/2013 | Liau | G06F 17/40 |
| | | | 707/709 |
| 2013/0182959 A1* | 7/2013 | Thrasher | G06T 5/003 |
| | | | 382/195 |
| 2013/0197936 A1 | 8/2013 | Willich | G06Q 50/22 |
| 2013/0259297 A1* | 10/2013 | Knudson | G06K 9/228 |
| | | | 382/103 |
| 2014/0032406 A1* | 1/2014 | Roach | G06Q 20/042 |
| | | | 705/42 |
| 2014/0089145 A1* | 3/2014 | Sunkada | G06Q 30/02 |
| | | | 705/26.63 |
| 2014/0092260 A1* | 4/2014 | Escobedo | H04N 5/23245 |
| | | | 348/207.1 |
| 2014/0176733 A1* | 6/2014 | Drooker | G06Q 50/01 |
| | | | 348/207.1 |
| 2014/0188835 A1 | 7/2014 | Zhang | G06F 17/2705 |
| 2014/0237405 A1* | 8/2014 | Wu | G06F 3/04845 |
| | | | 715/765 |
| 2014/0325484 A1* | 10/2014 | Gillaspie | G06F 11/3684 |
| | | | 717/124 |
| 2014/0344261 A1* | 11/2014 | Navta | G06F 16/951 |
| | | | 707/723 |
| 2014/0380142 A1* | 12/2014 | Mikutel | G06F 17/24 |
| | | | 715/234 |
| 2015/0074609 A1* | 3/2015 | Lanzkron | G06F 3/04842 |
| | | | 715/838 |
| 2015/0235297 A1* | 8/2015 | Cheung | G06Q 30/0631 |
| | | | 705/26.7 |
| 2016/0142358 A1* | 5/2016 | Zunger | G06Q 50/01 |
| | | | 709/206 |
| 2016/0171162 A1* | 6/2016 | Wang | G06F 16/955 |
| | | | 715/719 |
| 2016/0267484 A1* | 9/2016 | Smoley | G06Q 20/4016 |
| 2016/0373456 A1 | 12/2016 | Vermeulen | G06F 16/25 |
| 2017/0017648 A1* | 1/2017 | Pearlman | G06K 9/4671 |
| 2017/0060368 A1* | 3/2017 | Kochura | G06F 9/451 |
| 2017/0102693 A1 | 4/2017 | Kidd | G05B 19/41865 |
| 2017/0256173 A1 | 9/2017 | Burford | G09B 5/125 |
| 2017/0330195 A1* | 11/2017 | Lange | G06F 3/0486 |
| 2017/0344646 A1 | 11/2017 | Antonopoulos | H04L 9/008 |
| 2017/0371881 A1* | 12/2017 | Reynolds | G06F 16/256 |
| 2018/0121614 A1* | 5/2018 | Connely, IV | G16H 40/20 |
| 2018/0158146 A1 | 6/2018 | Turner | G06Q 40/02 |
| 2018/0210725 A1* | 7/2018 | Vaindiner | G06F 8/65 |
| 2018/0218643 A1* | 8/2018 | Wexler | G06K 9/00442 |
| 2018/0330329 A1* | 11/2018 | Anima | G06Q 10/107 |
| 2018/0359107 A1* | 12/2018 | Asher | G06K 9/3266 |
| 2018/0367557 A1 | 12/2018 | Brown | H04L 63/1425 |
| 2019/0012390 A1 | 1/2019 | Nishant | G06N 20/00 |
| 2019/0095255 A1* | 3/2019 | Anima | G06F 9/54 |
| 2019/0179820 A1 | 6/2019 | El Kaed | G06F 16/2471 |
| 2019/0180757 A1 | 6/2019 | Kothari | G10L 17/005 |
| 2019/0237203 A1* | 8/2019 | Schwabl | G06Q 10/1095 |

OTHER PUBLICATIONS

U.S. Appl. No. 16/387,016, filed Apr. 17, 2019, Hasija et al.
Office Action issued in U.S. Appl. No. 16/387,016, dated Jun. 25, 2019 (11 pgs).
Office Action issued in U.S. Appl. No. 16/363,897, dated Sep. 9, 2019 (38 pgs).
Morid et al. "Supervised Learning Methods for Predicting Healthcare Costs: Systematic Literature Review and Empirical Evaluation", 2018, AMIA Annu Symp Proc. pp. 1312-1321.
Wang et al. "Detecting Transportation Modes Based on LightBGM Classifier from GPS Trajectory Data", 2018 26th International Conference on Geoinformatics, Kunming, 2018, pp. 1-7.
Zhang et al. "Health reform and out-of-pocket payments: lessens from China", Health Policy and Planning, vol. 29, Issue 2, Mar. 2014, pp. 217-226, https://doi.org/10.1093/heapol/czt006.
Iyengar et al. "A Trusted Healthcare Data Analytics Cloud Platform", 2018 IEEE 38th International Conference on Distributed Computing Systems (ICDCS), Vienna, 2018, pp. 1238-1249.
International Search Report and Written Opinion issued in application No. PCT/US20/16849 dated Apr. 23, 2020 (10 pgs).
"Point of Care Integration Options", Arcadia, https://ihpsocal.org/wp-content/uploads/2019/01/3-Arcadia-Point-of-Care-Integration-Options.pdf, publication date unknown, accessed Jul. 8, 2021, 11 pgs.

* cited by examiner

AUTOMATIC VISUAL DISPLAY OVERLAYS OF CONTEXTUALLY RELATED DATA FROM MULTIPLE APPLICATIONS

CROSS REFERENCE TO RELATED APPLICATION

This application claims benefit of Indian Provisional Application Serial No. 201921005335 filed Feb. 11, 2019, the entire disclosure of which is incorporated herein by reference.

FIELD OF THE DISCLOSURE

The present disclosure is generally related to computing displays and information retrieval, and more particularly is related to systems and methods for automatic visual display overlays of contextually related data from multiple applications.

BACKGROUND OF THE DISCLOSURE

In modern corporate environments, all departments and organizations strive to achieve high efficiency operation. Information Technology (IT) tools, including computer applications and software programs, play a significant role in driving these efficiencies with appropriate data captures, symmetry of information across organization, better planning, and data analysis for process improvements. It has been observed that most small organizations utilize four to five IT tools on a regular basis, while mid-sized organizations commonly use 10 to 15 IT tools, and large organizations often use 50 to 100 IT tools. The sheer volume of IT tools used is not just a product of bad IT tool purchasing decisions, hut it also stems from the fact that no single IT tool is perfectly designed to solve for all organizational workflows required.

The impact on a human employee using multiple IT tools is often usage and alert fatigue. For example, many employees have to use three to four tools to complete their daily work, and commonly each tool will have its own credentials to remember, such as user identification (ID) and a password. These credentials must be entered initially upon use of the IT tool and often re-enteral if the employee is not active with that particular IT tool for a predetermined period of time. The use of these three to four tools on a daily basis can make it difficult for employees to focus and concentrate on the task at hand. Switching between the IT tools may also cause the employee to miss or neglect important alerts or notifications generated from the IT tools. One solution to this problem is found in single sign-on technology, which allows a user to have a single ID and password which can be used across multiple IT tools. Single sign-on technology has solved some of the problem with IT tool fatigue because the user only needs to remember one set of credentials, not different credentials, each with their own username and passwords.

However, even with single sign-on technology, employees required to use multiple IT tools are still prone to experiencing fatigue and burnout from using the different graphical user interfaces (GUIs) from each IT tool, some of which have multiple screens, tabs, or other visual interfaces. In order to complete a task, it is not uncommon for an employee to need to navigate back and forth between these various interfaces on the various IT tools to compile the required information. Moreover, with the increasing use of data stored in electronic form, such as, for example, electronic medical records (EMRs), the exposure of employees to these multiple IT tools on a daily basis is only growing.

As an example of this problem, within the healthcare industry physicians have reported huge burnout in using EMR software or electronic health records (EHR) software during a patient's visit. It has been found that in a 10 minute patient visit with the physician, as much as seven (7) minutes of that time are spent with the physician using the EMR or EHR software. This usage of the EMR or EHR software, while not explicitly required, is implicitly necessitated in order for the physicians to document their work, since physicians don't get paid on just the medical work they have performed, but also on the documentation of the medical work they have completed. Moreover, this use of the EMR or EHR software during a patient's visit is only growing. More and more of the relevant data a physician uses is in electronic form. And, physicians are constantly striving to provide better medical care to their patients, which requires them to look for additional information about the patient from different electronic sources, such as, for example, hospital records, opioid abuse databases, and population health tools. Even with using a single sign-on system, the time allotted for a physician's visit with a patient simply does not allow the physician sufficient bandwidth to open multiple software tools to access the various data often required for the physician to provide the highest quality healthcare to the patient.

Thus, a heretofore unaddressed need exists in the industry to address the aforementioned deficiencies and inadequacies.

SUMMARY OF THE DISCLOSURE

Embodiments of the present disclosure provide systems and methods for automatic visual display overlays of contextually related data from multiple applications are provided. Briefly described, in architecture, one embodiment of the method, among others, can be broadly summarized by the following steps: capturing an image of at least a portion of a graphical user interface (GUI) of a first application visually displayed on a computerized display device; identifying at least one primary contextual data point within the captured image; searching for at least one secondary data point in at least a second application, wherein the at least one secondary data point is contextually relevant to the primary contextual data point; fetching the at least one secondary data point from the second application; and visually displaying a panel on the computerized display device concurrently with at least a portion of the GUI of the first application, wherein the panel includes the at least one secondary data point.

The present disclosure can also be viewed as providing a computer-implemented system tor automatically overlaying computerized visual display's based on contextually related data from multiple applications. Briefly described, in architecture, one embodiment of the system, among others, can be implemented as follows. The computer-implemented system has a processor wherein the processor is configured to execute the steps of: capture an image of at least a portion of a graphical user interface (GUI) of a first application visually displayed on a computerized display device; identify at least one primary contextual data point within the captured image; search for at least one secondary data point in at least a second application, wherein the at least one secondary data point is contextually relevant to the primary contextual data point; fetch the at least one secondary data point from the second application; and visually display a panel on the computerized display device concurrently with at least a portion of the GUI of the first application, wherein the panel includes the at least one secondary data point.

The present disclosure can also be viewed as providing a system for automatically overlaying computerized visual displays based on contextually related data from multiple, separate computerized applications. Briefly described, in architecture, one embodiment of the system, among others, can be implemented as follows. A computerized device has a graphical user interface (GUI) visually displaying a first application. An image of at least a portion of the GUI of the first application is captured, wherein at least one primary contextual data point within the captured image is identified. At least one secondary data point in at least a second application is identified. The second application is separate from the first application. The at least one secondary data point is contextually relevant to the primary contextual data point. The at least one secondary data point is fetched from the second application. A panel is visually displayed on the GUI of the computerized device concurrently with at least a portion of the visually displayed first application, wherein the panel visually displays the at least one secondary data point.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 7-12 are illustrations of a computerized display device of the system for automatically overlaying computerized visual displays based on contextually related data from multiple applications, in accordance with the first exemplary embodiment of the present disclosure.

DETAILED DESCRIPTION

To improve upon the aforementioned shortcomings in the art, the subject disclosure is directed to automatically overlaying computerized visual displays based on contextually related data from multiple applications. As described herein further, the present disclosure allows for users of multiple IT tools to maintain a constant visual presence with one IT tool while automatically retrieving contextually relevant data from one or more other IT tools. The ability to automatically retrieve contextually-related data from IT tools without needing to visually depart from a currently-displayed IT tool may allow employees who are required to use multiple IT tools to more efficiently gain the data they need in order to complete their job. The efficiency gained with the present disclosure may alleviate IT tool fatigue and burnout, resulting in a better experience for the employee without limiting their access to the needed data. The subject disclosure may be applicable to any industry which uses IT tools, for example, the healthcare and medical industries, which are used as a primary example herein.

Figure 1:
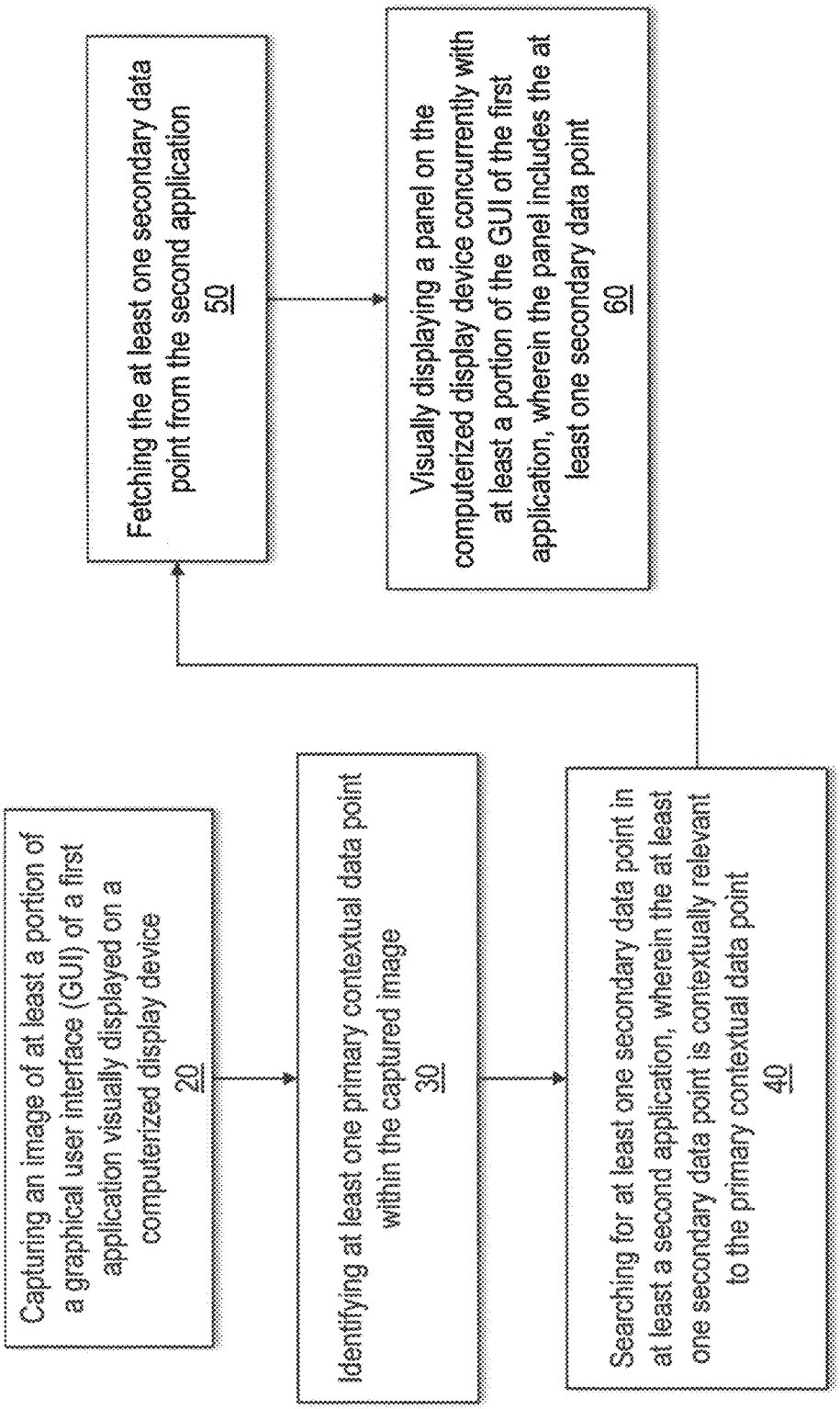
FIG. 1 is a flow chart illustrating a method for automatically overlaying computerized visual displays based on contextually related data from multiple applications, in accordance with a first exemplary embodiment of the present disclosure.

FIG. 1 is a flow chart illustrating a method JO for automatically overlaying computerized visual displays based on contextually related data from multiple applications, in accordance with a first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure. The method may further include any other features, components, or functions disclosed relative to any other figure of this disclosure.

The method 10 for automatically overlaying computerized visual displays based on contextually related data from multiple applications, which may be referred to herein simply as 'method 10' may be employed with one or more user computing devices which have a visual display device. The display device may include, for example, a display screen integral with the computing device or an external display screen, and may include, for example, display screens of laptop computers, tablet computers, smartphones, or external monitors in communication with desktop computing devices, among others.

Step 20 includes capturing an image of at least a portion of a GUI of a first application visually displayed on a computerized display device. The GUI may be any visual display interface produced or provided by the first application, which may include any type of software application or program. For instance, the GUI may be a data screen on the first application which displays one or more data points about a particular topic or topics. The image captured may include all or part of the GUI, including portions of the GUI which may or may not be visually identifiable by the human user of the computing device, e.g., if a portion of the GUI is currently off-screen. The image may be captured using any digital image capture or acquisition technique, such as digitization, with snapshots, screengrabs, screenshots, or others.

In one example, a computer vision technique may be used to constantly grab snapshots of the GUI, or take snapshots at predetermined intervals, such that immediate, automatic processing of the image data can be done. Computer vision techniques may allow computers to gain a high-level understanding from digital images or videos. The computer vision technique may imitate the natural instinct of a human provider reading information on the display screen, such that it can effectively automate tasks that the human visual system can do. It may also eliminate the need to integrate with each and every service and tool used by the providers and health system, since it may effectively fill in the data and/or processing otherwise provided by services and tools in the industry. As an example of the computer vision technique within the healthcare field, the first application may be an enterprise resource planning (ERP) program such as PEOPLESOFT® which is used by a physician to manage patients, where an interface listing one or more patients, visually displayed to the physician, may be image-captured, in all or part.

Computer vision tasks may include methods for acquiring, processing, analyzing and understanding digital images, as well as tasks for the extraction of high-dimensional data from the real world in order to produce numerical or symbolic information, for example, in the form of decisions. For these tasks, various algorithms may be used across industries, depending on the different use-cases, to achieve optical character recognition (OCR), video detection, image recognition, object recognition, motion estimation, or others. Specific algorithms which may be employed may include, but are not limited to:

OTSU's Algorithm: OTSU's Algorithm, also known as Otsu's method, is one the most fundamental techniques used in OCR and detection. The algorithm is used to automatically perform clustering-based image thresholding, or, the reduction of a gray level image to a binary image. The algorithm assumes that the image contains two classes of pixels following bi-modal histogram (foreground pixels and background pixels), it then calculates the optimum threshold separating the two classes so that their combined spread (intra-class variance) is minimal, or equivalently (because the sum of pairwise squared distances is constant), so that their inter-class variance is maximal. Consequently, OTSU's algorithm is roughly a one-dimensional, discrete analog of Fisher's Discriminant Analysis. Otsu's method is also directly related to the Jenks optimization method.

K-Nearest Neighbor's Algorithm: Nearest neighbor classifiers such as the k-nearest neighbor's algorithm are used to compare image features with stored glyph features and choose the nearest match.

Adaptive Recognition Algorithms: adaptive recognition uses the letter shapes recognized with high confidence on the first pass to recognize better the remaining letters on the second pass. This may be advantageous for unusual fonts or low-quality scans where the font is distorted (e.g. blurred or faded).

Machine Learning/Neural Network Algorithms: All the above algorithms and models, including OTSU's Algorithm, the K-Nearest Neighbor's Algorithm, and the Adaptive Recognition Algorithms may be combined with a machine learning technique. This may provide a rich learning dataset which can be improved multi-fold when used in a neural network to improve the accuracy of the whole solution in a continuous and incremental fashion.

It is noted that other algorithms, models, and forms of processing which are not explicitly recognized herein may also be used, all of which are considered within the scope of the present disclosure.

At step 30, at least one primary contextual data point is identified within the captured image. Identification of the contextual data point may be achieved by various techniques, such as optical character recognition, using pixel comparison and matching, feature extraction, or other methods. Traditional OCR may be used but it traditionally has a low accuracy rate. To improve the accuracy, it is possible to use neural network-enabled OCR which has proven to provide far higher accuracy and more predictability than traditional OCR. The method may include gaining an understanding of the primary data point in the first application through image recognition using deep learning models, machine learning techniques, or other computer vision techniques or algorithmic processing. The primary contextual data point may be a single data point or a collection of data points which are related to one another, whereby a particular context can be gained from the data point or points. Generally, the primary contextual data point is a type of categorical or high-level data which can be used to gain further information about the particular context. Continuing with the previous healthcare example, the contextual data point may include a patient's identity, including their name, their date of birth, their patient ID number, and/or other relevant information about the patient, which can be used to find other information about the patient.

The other information which can be gained from the primary contextual data point may be referred to as a secondary data point. Step 40 includes searching for at least one secondary data point in at least a second application, where the at least one secondary data point is contextually relevant to the primary contextual data point. The second application may be any other computer software application or program, or IT tool, which may be used. The second application is a distinct and separate computer program from the first application, in that, the second application contains data which is not readily identifiable from the GUI of the first application. In some situations, the first and second applications may be interrelated to some degree, such as by being able to communicate directly with one another, e.g., where one application can transmit and/or receive data to/from the other application, or the applications may be subsets of an overarching single application. Searching for the secondary data point may be achieved by various techniques such as with REST API requests among others, where appropriate searching and data retrieval is carried out through a backend application. It is noted that the user need not log-in to the secondary application for each query or search completed. Rather, the user may be able to provide the computerized method with the appropriate login parameters such that the second application can be accessed as needed without further user interaction.

The secondary data point may be contextually related to the primary contextual data point through any conditional relationship, such that the secondary data point has an association with the focal event of the primary contextual data point. For example, if the primary contextual data point is a patient's identity, such as their name, their date of birth, their patient ID number, per the previous example, the secondary data point may include specific EMR data about the patient, such as a record of their medical visits, medical tests which have been conducted on the patient, medications they are taking, or other similar information. The secondary data point may also include other information, such as doctors or relatives associated with the patient, population-wide data correlated to the patient's age, demographics, or health status, or the secondary data point may include any other contextually-relevant information to the primary data point which may provide further context or information about the primary data point, all of which are considered within the scope of the present disclosure.

Step 50 includes fetching the at least one secondary data point from the second application. Here, the secondary data point which is retrieved from the second application is transmitted to a local file system where the information can be stored for future displaying or retrieval. The secondary data point may further be formatted or otherwise configured to meet any particular formatting or display parameters.

Step 60 includes visually displaying a panel on the computerized display device concurrently with at least a portion of the GUI of the first application, wherein the panel includes the at least one secondary data point. The displaying of the panel may include an outslide panel which is overlaid on the GUT of the first application, whereby it is depicted on the display device proximate to the GUI of the first application. For example, the panel may include a GUI which is smaller in dimension than the GUI of the first application, and which is positioned to the left, right, above, or below the GUI of the first application, such that the panel and the GUI of the first application, or at least a portion of the GUI of the first application, are concurrently or simultaneously visible on the display screen to the user. The panel may be positioned on top of the GUI of the first application, or adjacent to the GUI of the first application, whereby the first application's GUI is lessened in size to accommodate the panel. In this position, the user of the computer may be able to visually see both the data from the original GUI of the first application and the secondary data point(s) contained on the panel at the same time, such that it is easy and efficient for a user to gain an understanding of the information from both the first application and the second application. The method may leverage the deep integration with the user's computing device operating system (OS), e.g., Windows/Mac/Android/iOS, and based on the user's preference already associated with the OS, automatically machine configure information for display. The method may integrate this information into the display and manipulate the GUI to show the relevant information. The OS of the user's computing device may provide permissions required by the applications to allow for the modification on the GUI.

It is noted that the format of the secondary data point displayed on the second panel may vary, depending on the design of the system. For example, the secondary data point may include textual information, numerical data, visual data, such as graphs and charts which the user can visually view to obtain more information, or it may include actionable features such as other data tools, calendars, icons for performing other actions, links to further information, menus, or any other type of data which the user can select to perform a further action. Thus, the display of the secondary data point may include both visual and actionable data features. The specific type of data displayed on the panel may be determined based on the industry or field in which the method is being used, all of which are considered within the scope of the present disclosure.

For security purposes and otherwise, it may be desirable for the captured image or snapshot from the first application and the recognized and identified contextual information sets of the secondary data points to be destroyed as soon as the image recognition is carried out and context of the application is established. This may ensure that historical data retrieved by the method is not subject to inadvertent or malicious retrieval by unauthorized parties. Other security measures may also be employed to ensure safe operation of the method and to maintain the privacy and/or confidentiality of any information accessed.

Figure 2:
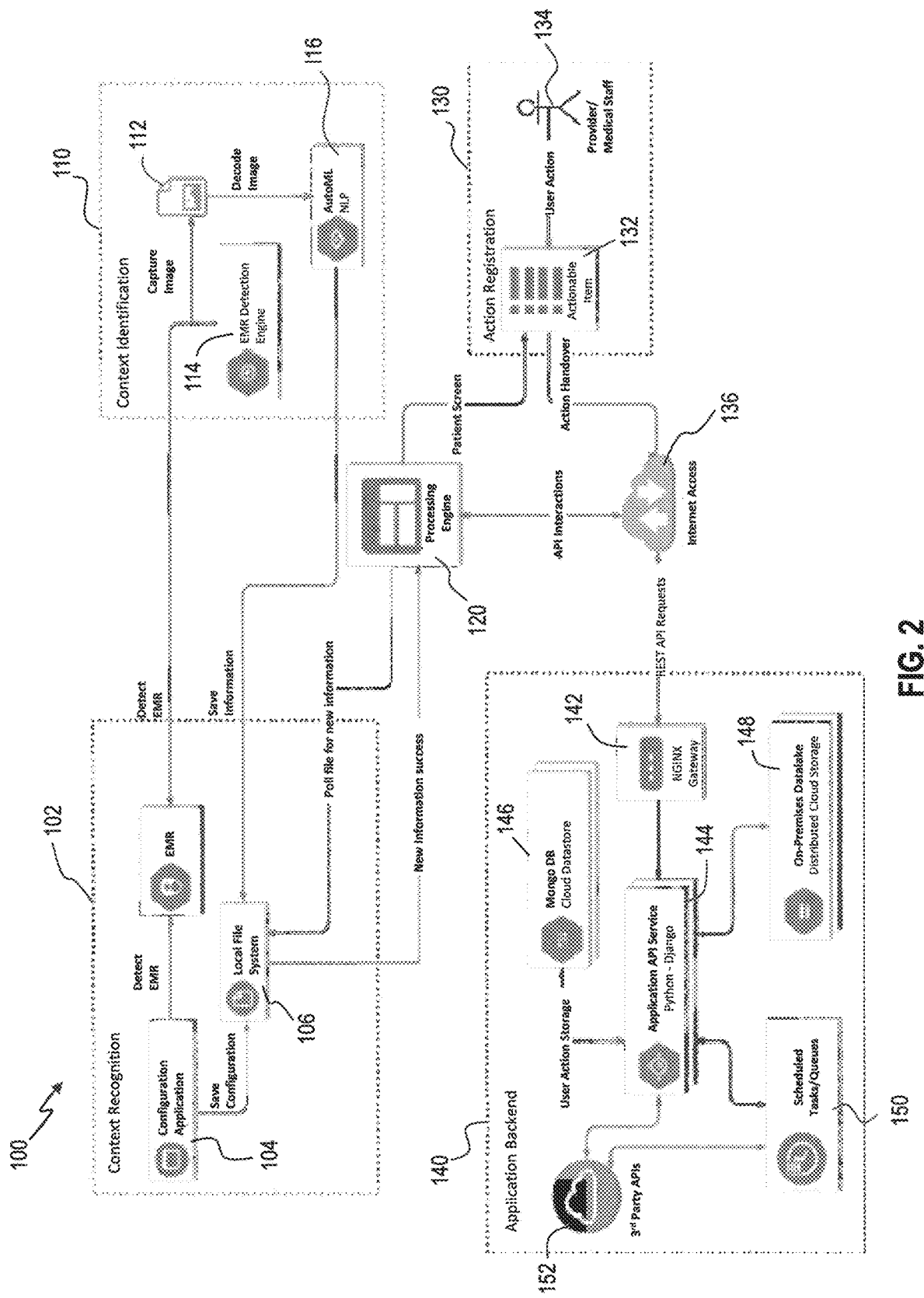
FIG. 2 is a diagrammatical illustration of a system for automatically overlaying computerized visual displays based on contextually related data from multiple applications, in accordance with the first exemplary embodiment of the present disclosure.

FIG. 2 is a diagrammatical illustration of a system for automatically overlaying computerized visual displays based on contextually related data from multiple applications 100, in accordance with the first exemplary embodiment of the present disclosure. In particular, FIG. 2 illustrates a diagrammatical architecture of the system 100 which can be used to employ the method described relative to FIG. 1. As shown, a context recognition module 102 includes a configuration application 104 which may be used to set configuration parameters. For example, the configuration application 104 may include configurability built-in to determine or identify input parameters pertaining to the images captured, such as what portion or portions of the GUI to take snapshots of, the size and/or quality of the snapshots, the interval of image capture, and other. The configuration may be saved to a local file system 106. The configuration application 104 is connected to a context identification module 110 which includes an image capture module 112 or image recognizer, a data detection engine 114 for detecting data (such as EMR data), and a machine learning model module 116. The image recognizer 112 captures an image of pane of the GUI which contains the primary data points, such as demographic details of a patient. The data is detected by the data detection engine 114 from the captured image and it is transmitted to the context recognition module 102, where the context recognition module 102 fetches the name, date of birth, gender, and/or other information from the captured image. The machine learning model module 116 may decode the captured image, with the resulting data being transmitted to the local file system 106 in the context recognition module 102 where it is saved.

A processing engine 120 is in communication with the local file system 106, whereby it can poll file for new information which has been saved in the local file system, and the requested new information can be transmitted from the local file system 106 to the processing engine 120. The processing engine 120 is also in communication with an action registration module 130 and an application backend module 140. When an actionable item is identified at block 132, an entity or patient (in the case of healthcare data) may be screened and the data pulled from the local file system 106 by the processing engine 120 may be transmitted to the actionable item module 132. Here, a user 134, such as a medical provider or staff member, may access the actionable item module 132 to review and identify the information. For example, the physician may be able to view the information on a panel which is integrated into the display device concurrently with the GUI of an existing application the physician is using on the computer, as described relative to FIG. 1 and FIGS. 4-6.

The processing engine 120 may further facilitate API interactions through a network connection 136, such as the Internet, whereby REST (Representational State Transfer) API requests from the processing engine 120 may be transmitted to the application backend module 140. Action handovers may also be transmitted to the application backend module 140 or to other locations through the network connection 136. In the application backend module 140, the REST API requests are processing in a web server, such as a NGINX Gateway server 142. The data is transferred to an application API service module 144 which may operate using various programming languages and frameworks, such as Phython-Django. A cloud datastore 146 may be used to store user actions from the application API service module 144 and an on-premises datalake 148 within a distributed cloud storage system may be used to store data from the application API service module 144. A scheduled tasks and queues module 150 may communicate with the application API service module 144 for scheduling of actions to be performed and/or queues of requests, which may coordinate with various 3$^{rd}$ party APIs 152 as needed. The 3$^{rd}$ party APIs 152 may also have direct access to the application API service module 144.

It is noted that the system 100 may further include other hardware, software, or functionality beyond what is explicitly shown in FIG. 2. Additionally, it is noted that any specific references to particular programming languages, frameworks, algorithms, and other components may be substituted by similar features which art used within the industry, all of which are considered within the scope of the present disclosure.

Figure 3:
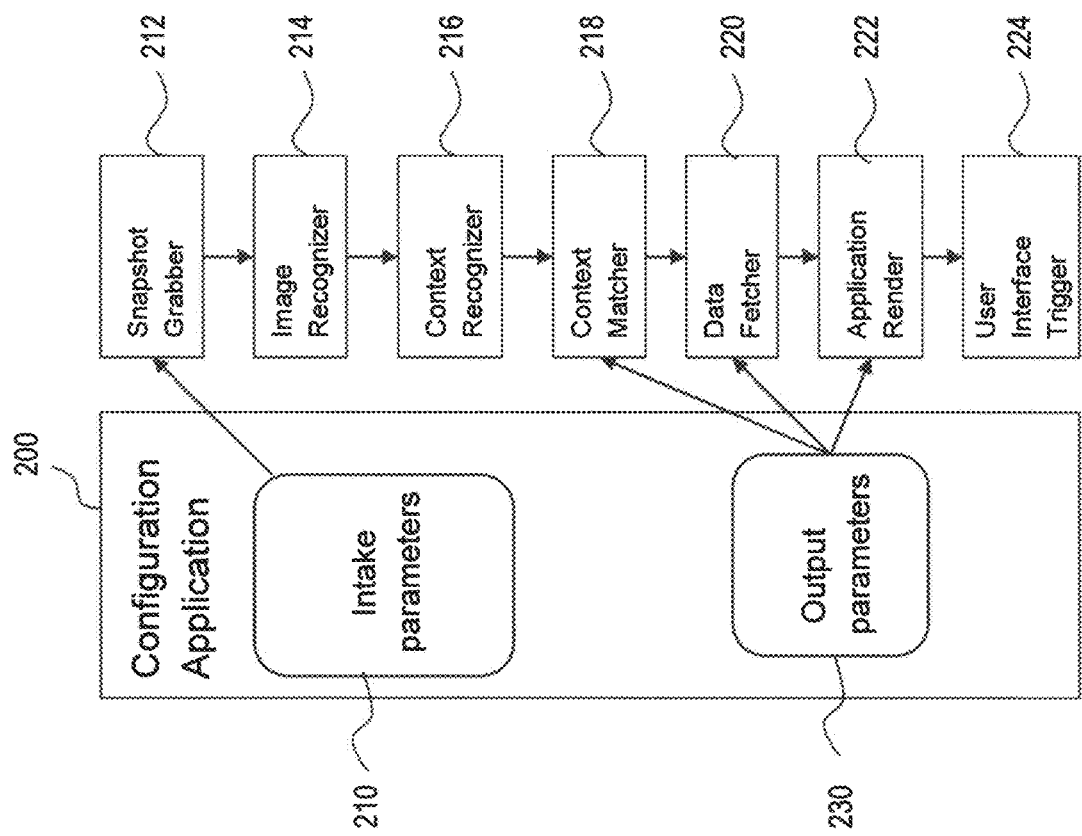
FIG. 3 is a diagrammatical illustration of a configuration application of the system for automatically overlaying computerized visual displays based on contextually related data from multiple applications, in accordance with the first exemplary embodiment of the present disclosure.

FIG. 3 is a diagrammatical illustration of a configuration application of the system 100 for automatically overlaying computerized visual displays based on contextually related data from multiple applications, in accordance with the first exemplary embodiment of the present disclosure. In particular, FIG. 3 illustrates a configuration module 200 where various intake parameters 210 and output parameters 230 are configured. For example, the configuration module may have configurability built-in to configure input parameters, like which snapshots to take and at what size, as well as output parameters such as a quantity or type of secondary data to display. The intake parameters 210 may include a snapshot grabber module 212 which is used to configure the image capture technique relative to the GUI or a part of the GUI, for example, what portion of the visual GUI is to be screen-grabbed. The image recognizer module 214 recognizes the image and pulls out the primary contextual data point, such as the name of a patient or other entity. The image recognizer module 214, as described relative to FIG. 2, may utilize one or more deep learning networks to recognize the image and convert text from the image. The context recognizer module 216 recognizes the context of the primary data point. The context recognizer module 216 may use a natural language processing unit which understands text extracted from image recognizer module 214 and identifies the primary contextual data points, such as people, dates, places, etc. separately from one another.

Next, the context matching module 218 matches the primary data point with data from a repository. For example, the context matching module 218 may match a patient's name or other identifying information with information from an internal datalake in which EMR, health claims data, and other data is stored. The context matcher module 218 may help to match the primary data point processed and identified in earlier step, e.g., the entity, person, date, place, etc., in the primary application with the secondary data point in the secondary application(s). The data fetcher module 220 fetches the data from the repository or another application or program. Here, the data fetcher module 220 may extract insights relevant to the context from the repository or datalake and present it to the user interface using the application rendering module 222. Accordingly, the application render module 222 may be used to configure the form, format, or parameters for displaying the fetched data. For example, the application render module 222 can be used to select which specific type of data is to be shown on the panel which outslides to the GUI of the primary application. Then, the user interface trigger module 224 may be used to display the selected data on the panel.

Figure 4:
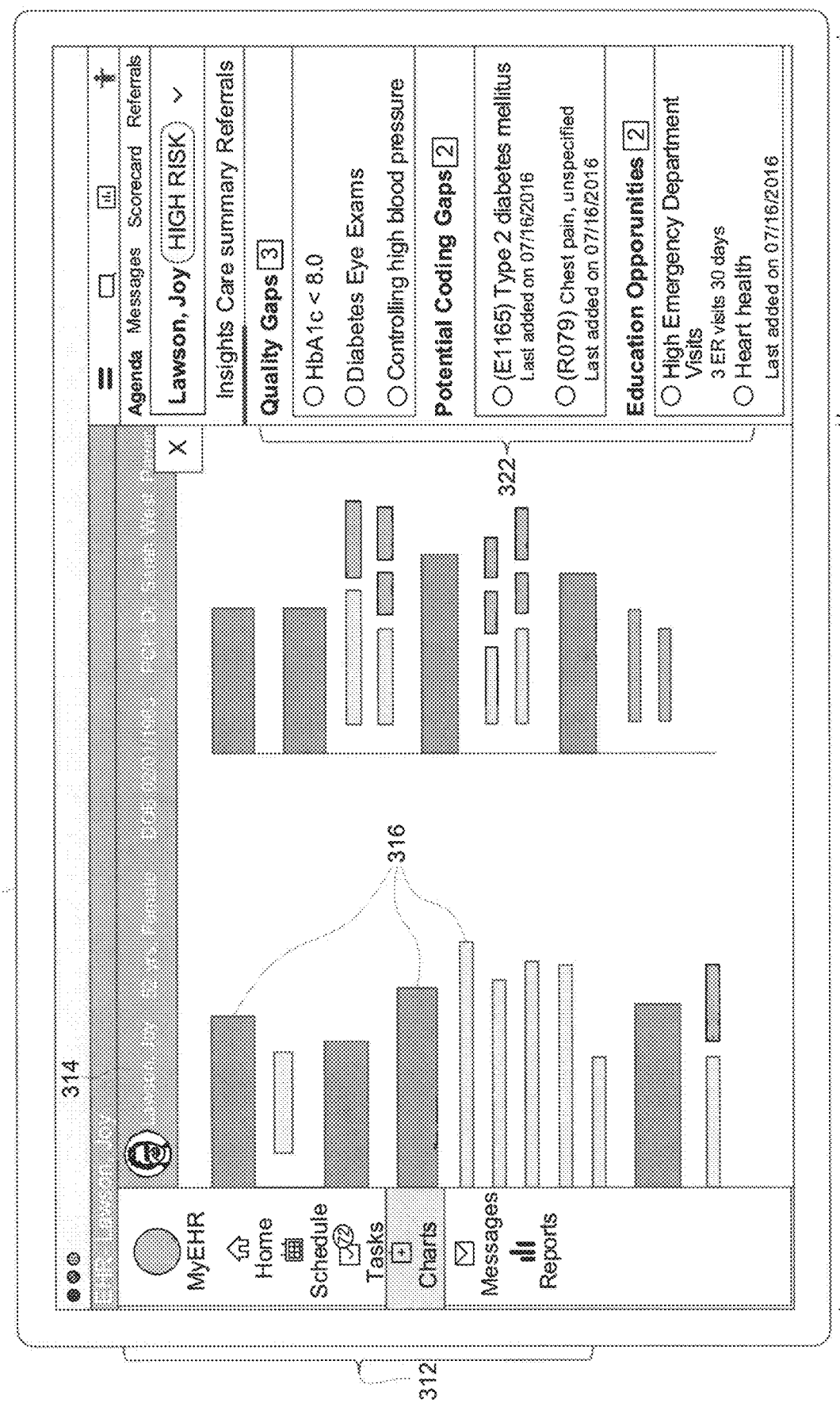
FIGS. 4-6 are illustrations of a computerized display device of the system for automatically overlaying computerized visual displays based on contextually related data from multiple applications, in accordance with the first exemplary embodiment of the present disclosure.
Figure 5:
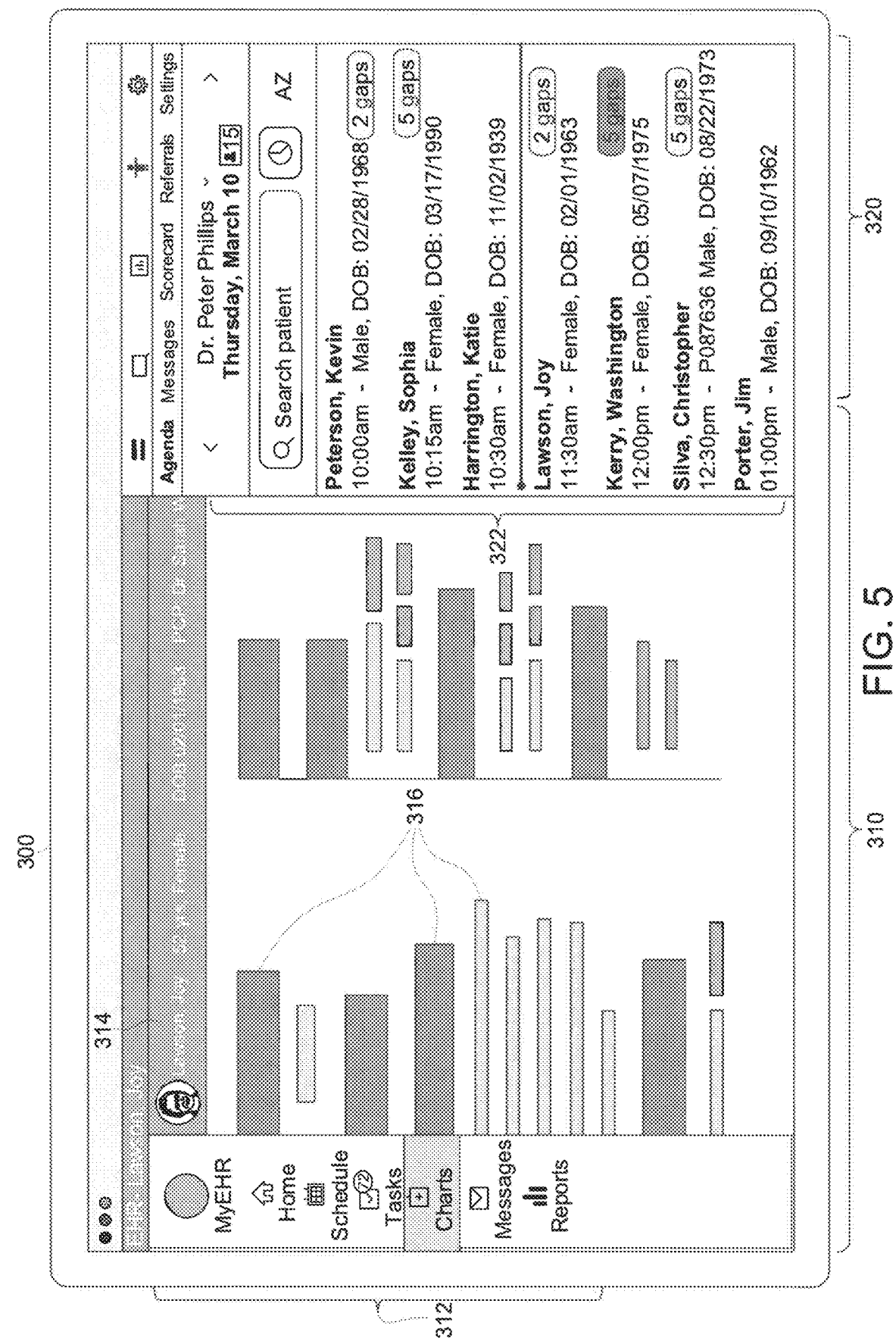
Figure 6:
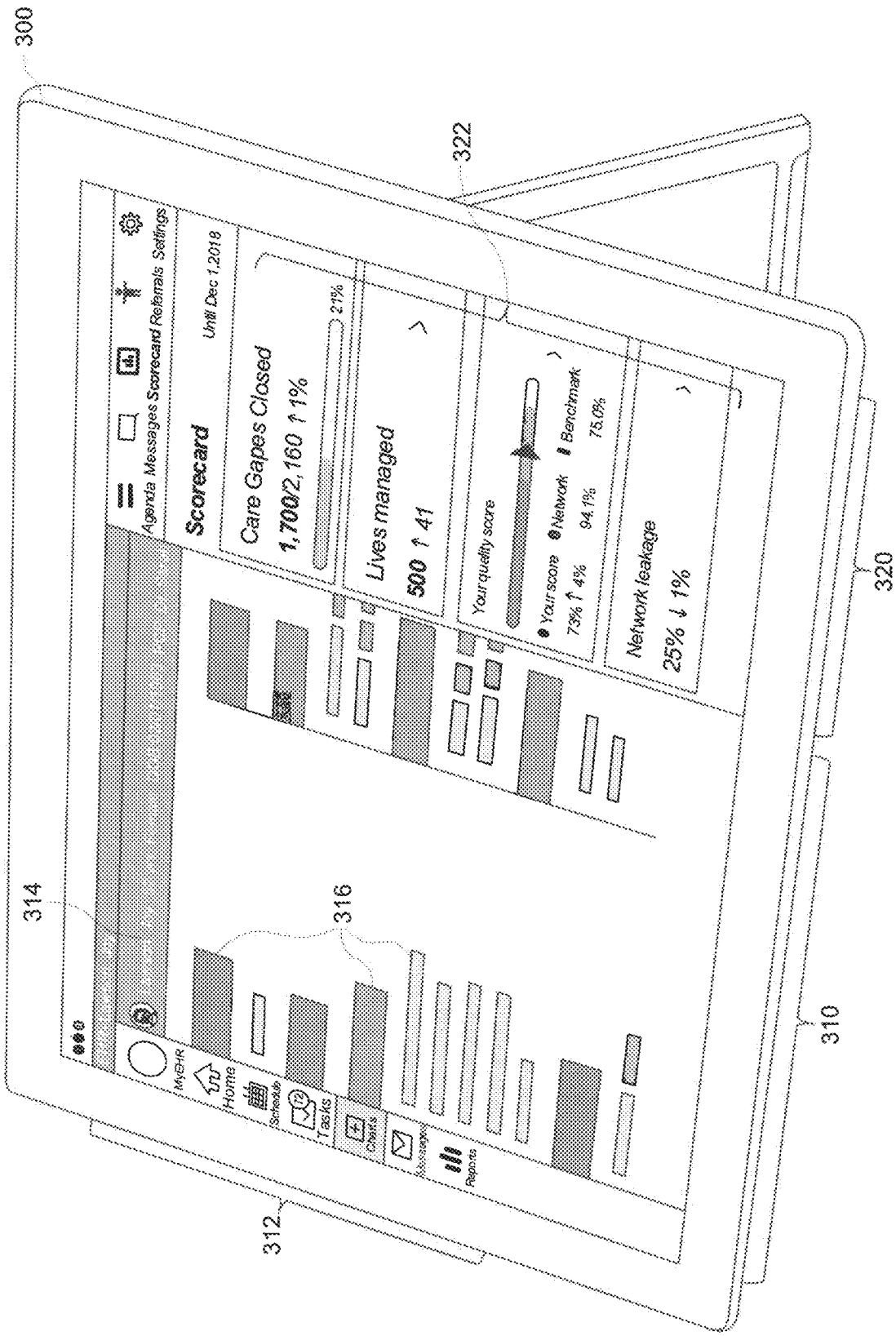

In one embodiment relevant to healthcare and medical data, the method includes setting the configuration for an EMR application. Then the image recognizer gets an image of a pane of the GUI of the first application which contains demographic details of a patient. The context recognizer then fetches name, date of birth, gender, or other primary data points from the image. The context matcher then compares the demographic data with an enterprise level master patient index and fetches a universal patient ID. The data fetcher then fetches care gaps, coding gaps, high utilization markers, dispensed/prescribed medications, and other such insights from health datalake. The fetched information in presented by the application render module, in cards layouts, such as depicted in FIGS. 4-6. The panel containing this secondary data slides out or pops out from a part of the display screen, such as the right hand side, and showcases the cards with insights rendered by application render module. Then, the user of the computing device can simultaneously or concurrently view information from the GUI of the first application and the secondary data points in the pane.

As specific visual interface examples, FIGS. 4-6 are illustrations of a computerized display device 300 of the system for automatically overlaying computerized visual displays based on contextually related data from multiple applications, in accordance with the first exemplary embodiment of the present disclosure. As shown in FIGS. 4-6, the display device 300 includes a GUI of a first application 310, such as a healthcare ERP platform which is used by physicians to manage a patient's EMR and health claims data. The first application 310 may also be other programs, such as an electronic medical record (EMR) program. In FIGS. 4-6, the ERP platform displayed on the GUI 310 may include various menus 312 which are selectable to provide the user with different tabulated screens of the application to display on the GUI, such as, for example, a home screen, a scheduling screen, a tasks screen, a chart screen, a messages screen, and a reports screen, among others. Here, the GUI of the first application displays primary contextual data points 314 about the user, such as a name (Lawson, Joy), and age and sex (52 yrs. Female), a date of birth (Feb. 1, 1963), and a primary care provider (Dr. Sarah West), among others. Other data 316, including additional primary data points, secondary data points, or other information may be visually depicted on the GUI (diagrammatically shown in block form for clarity).

Per the descriptions provided relative to FIGS. 1-3, when the method is applied to the GUI 310, an image of the GUI 310 may be captured and one or more primary data points 314 are identified. These primary data points are used to provide the secondary data points which are shown in panel 320. In the present example, the panel 320 may outslide from the right hand side of the display screen, such that it can be displayed concurrently with the GUI 310 of the base application. The panel 320 identifies the primary data point identified, the patient's name (Lawson, Joy), and includes various secondary data points 322 which have been automatically retrieved front secondary applications or IT tools without the user needing to navigate to them. The secondary data points 322 are contextually relevant to the primary data point. For example, the secondary data points 322 shown, which may include quality of care gaps which are identified, potential coding gaps, education opportunities, etc., are specific to the patient. Joy Lawson, and describe her specific medical insights.

It is noted that the panel 320 may include various tabulated screens or sub-screens, such that a user can navigate within the panel to achieve more information. For example, the panel shown in FIG. 4 depicts an agenda screen, a messages screen, a scorecard screen, a referrals screen, among others, and it further includes sub-screens therein, such as where the agenda screen includes tabs for insights, care summary, referrals, etc. FIGS. 5-6 depict the same display screen 300 but illustrate panels 320 with different secondary data points shown. For example, in FIG. 5, the secondary data points 322 include scheduling information for the physician, whereby be or she can see a patient's name and indicators of any healthcare gaps that patient may have. FIG. 6 illustrates a scorecard view on the panel 320 whereby the physician can see an overview of healthcare gaps, such as which have been closed, which remain active, and with scoring of quality.

It is noted that the secondary data points 322 displayed on the panel 320 may include the various data points identified, but may also include actionable items where the user can achieve further information. For example, in FIG. 4, the user (a physician) can select the various quality gap items, such as the HbA1c test or the Diabetes Eye Exams, and gain more specific information on these particular secondary data points. Various other configurations, options, and functionality with regards to the secondary data points may also be included, all of which are considered within the scope of the present disclosure.

Figure 7:
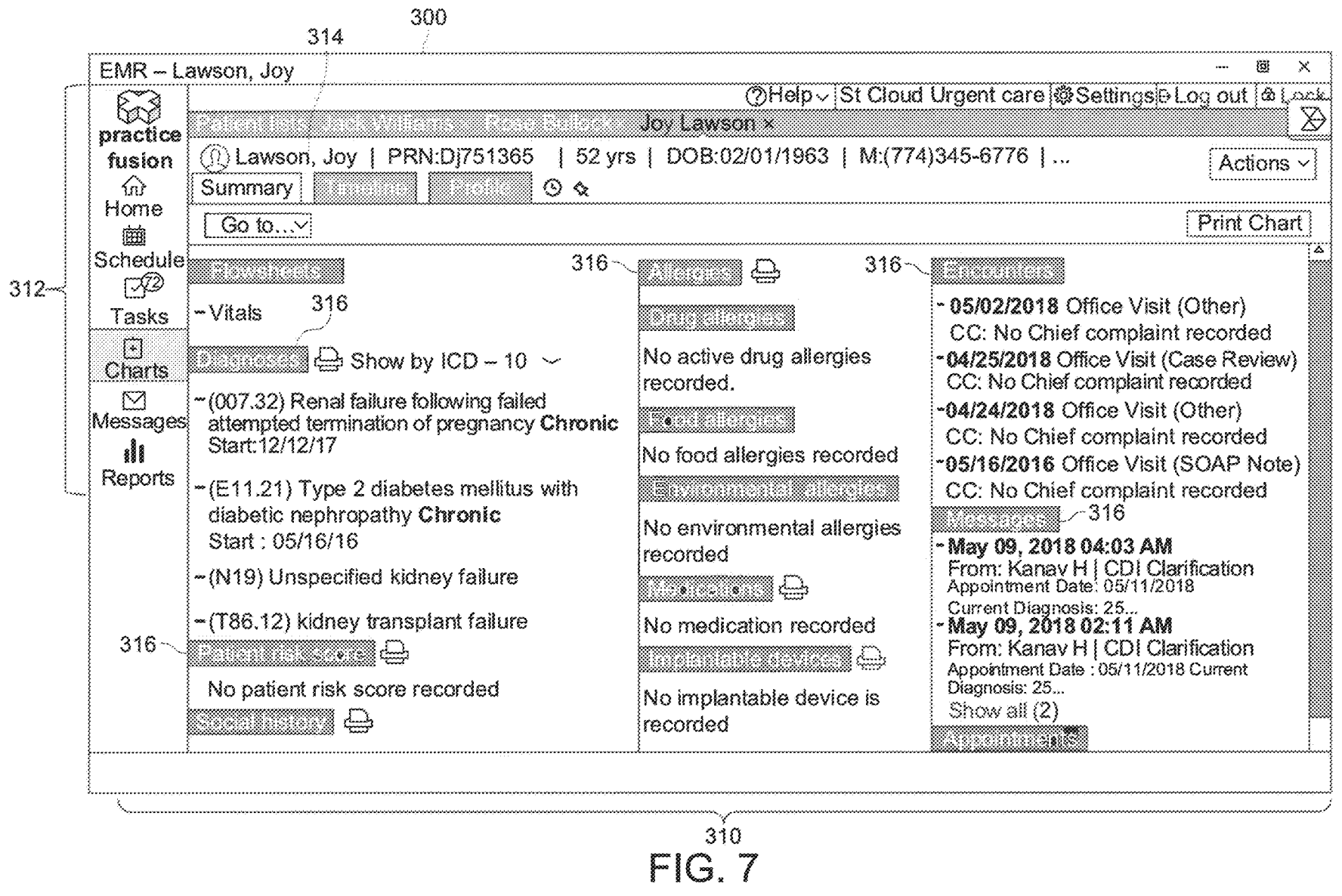

As more detailed examples of specific visual interface, FIGS. 7-12 are illustrations of a computerized display device 300 of the system for automatically overlaying computerized visual displays based on contextually related data from multiple applications, in accordance with the first exemplary embodiment of the present disclosure. With reference first to FIG. 7, a first application 310 is shown which depicts a screen of an EMR program. In the program, the visual interlace displays various menus 312 on the left-hand side of the screen, each of which is selectable to provide the user with different tabulated views of the application to display on the GUI. For example, the user can select a practice function screen, a home screen, a schedule screen, a tasks screen, a charts screen, a messages screen, and a reports screen, among others. Each of these screens displayable on the GUI is correlated to a selected primary data point 314, such as the patient, Joy Lawson. Other primary data points 314 may include an age, a date of birth, identification information, a particular medical condition, a diagnosis, or other information which may serve as a primary point of data about a particular individual, condition, or situation.

At the top of the screen, the patient's information may be provided and in the body of the screen other data points 316 are provided. These other data points 316 may include additional categorical information about the patient, which may be selectable and/or viewable by the user. For example, the user can select and view flowsheets, diagnoses, patient risks scores, history, allergies, medications, implantable devices, encounters or office visits, messages, and appointments, among others. Each of the data points 316 may have sub-data points with dates, medical codes, links to further information, forms, or reports, doctor notes, or other features.

Figure 8:
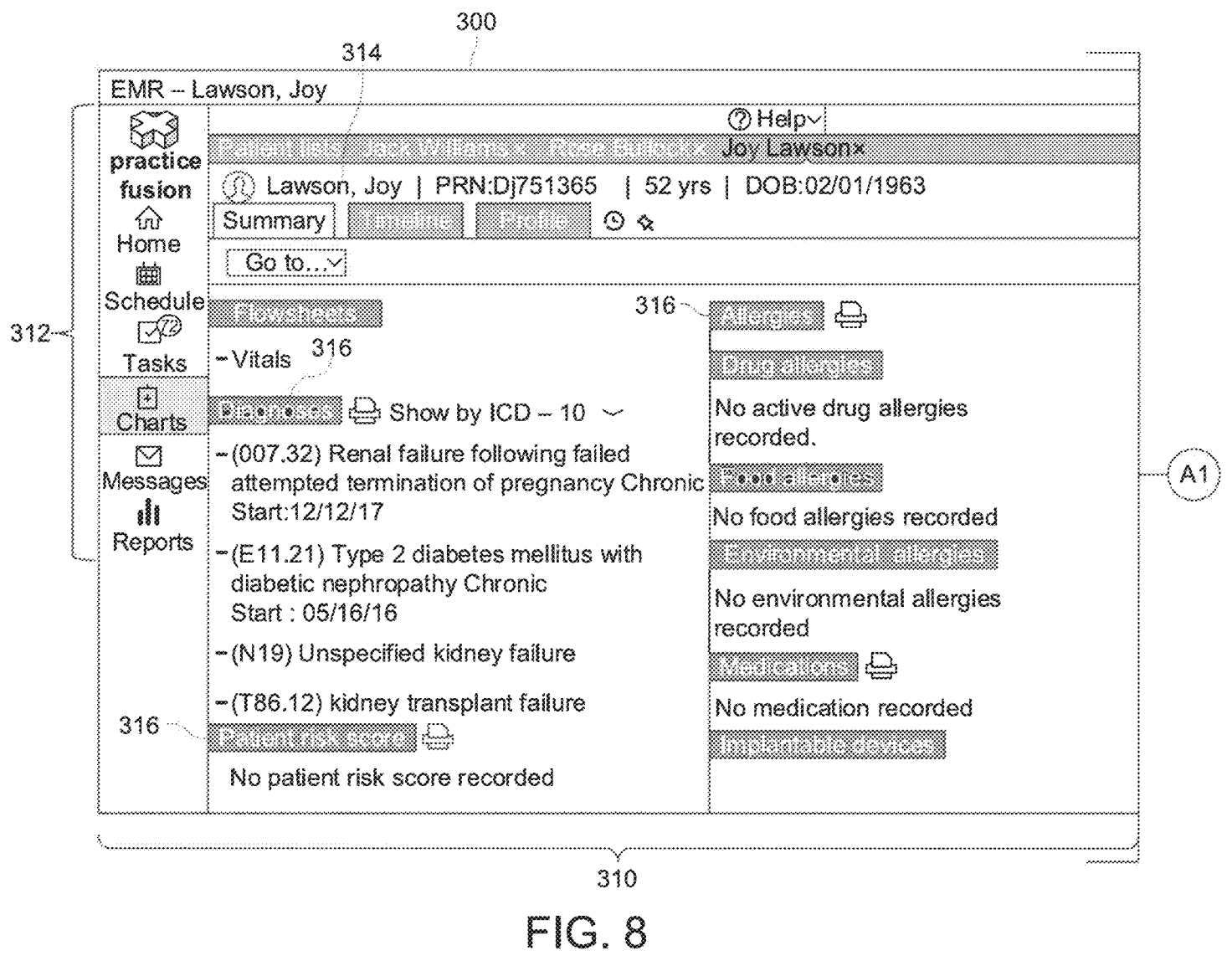
Figure 8:
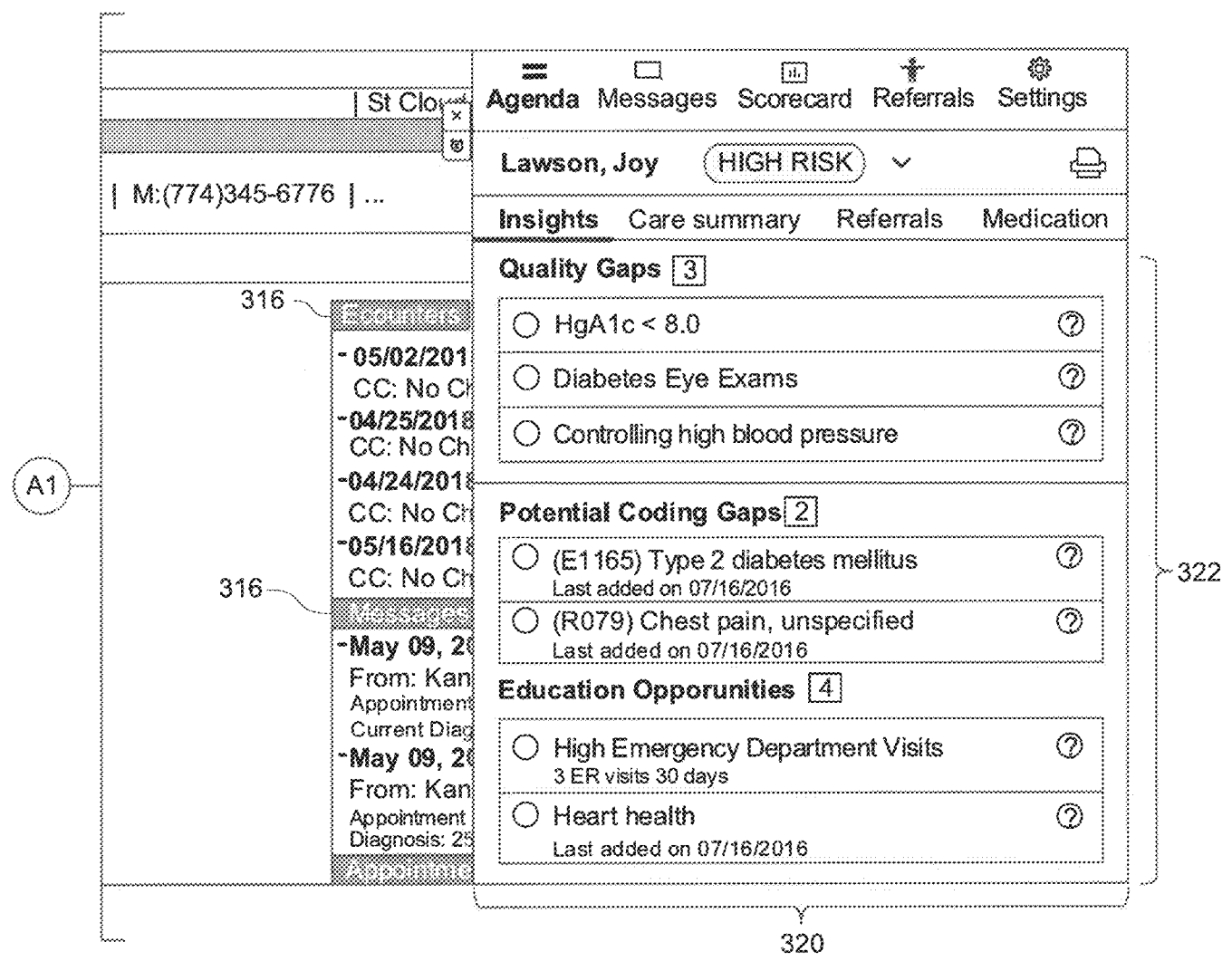
Figure 9:
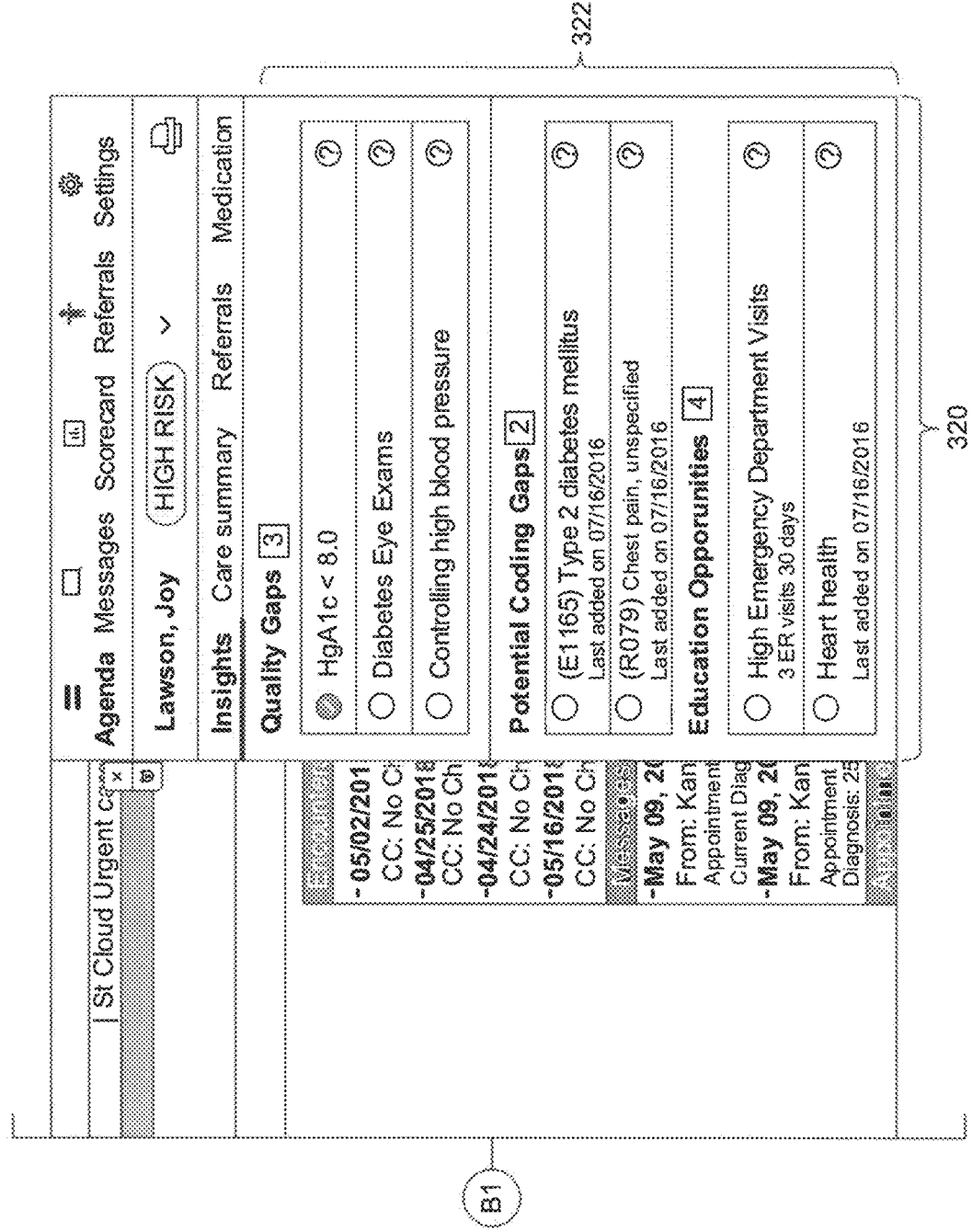

As can be seen in FIG. 7, due to the complexity of the data in the EMR program, the first application 310 may occupy all or substantially the entire GUI screen viewable to the user. However, when a user of the EMR program wishes to have more information about the patient or another data point, be or she may use the system and methodology described relative to FIGS. 1-3 to capture an image of the first application 310 and use the primary data points 314 to provide the secondary data points which are shown in panel 320, as is shown in FIGS. 8-9. Here, the primary data point is the name "Lawson, Joy" such that the panel 320 displays secondary data points 322 which correlate or correspond to Joy Lawson. The panel 320 may outslide from the right hand side of the display screen, e.g., move from the right hand side of the screen to partially cover the viewable screen of the first application 310, such that it can be displayed concurrently with at least a portion of the first application 310. The panel 320 identifies the primary data point identified, the patient's name (Lawson, Joy), and includes various secondary data points 322 which have been automatically retrieved from secondary applications or IT tools without the user needing to navigate to them.

The secondary data points 322 are contextually relevant to the primary data point. For example, the secondary data points 322 shown, which may include quality of care gaps which are identified, potential coding gaps, education opportunities, etc., are specific to the patient, Joy Lawson, and describe her specific medical insights. A user can navigate to one or more of these secondary data points 322 by clicking or otherwise selecting them, as is shown in FIG. 9 where the user has selected the Quality Gap "HgA1c" secondary data point 322. This allows the user to then retrieve more information about this specific secondary data point 322. The additional information may be displayed on the panel 320 or in another part of the GUI.

It is noted that the panel 320 may include various tabulated screens or sub-screens, such that a user can navigate within the panel to achieve more information. For example, the panel shown in FIGS. 8-9 depicts an agenda screen, a messages screen, a scorecard screen, a referrals screen, among others, and if further includes sub-screens therein, such as where the agenda screen includes labs for insights, care summary, referrals, etc.

Figure 10:
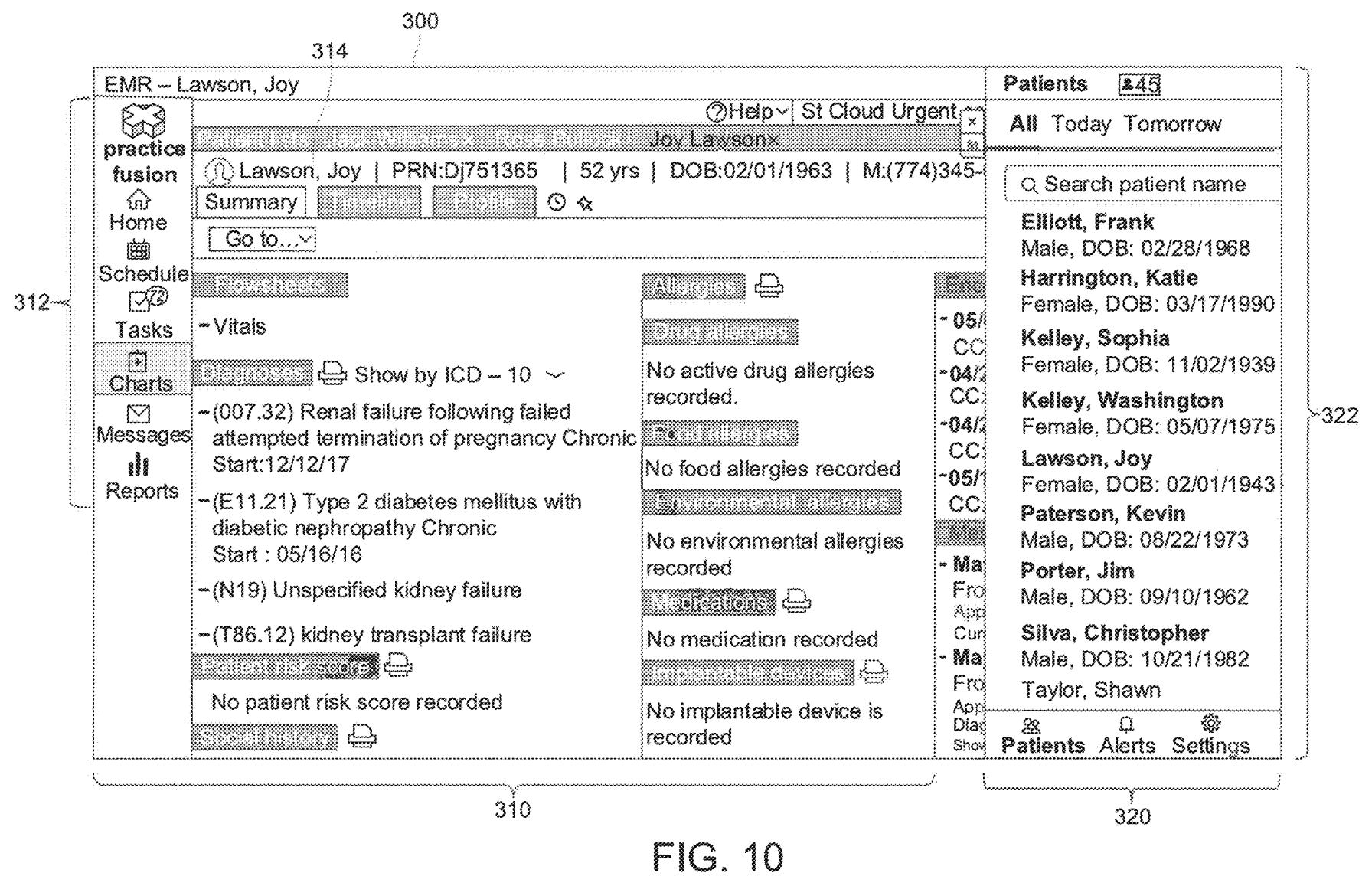

In FIG. 10, the first application 310 having the EMR program is shown with a panel 320 which displays a search feature. Here, panel 320 may be used to provide a searchable listing of patients or other primary data points 314. The panel 320 may display a search query box where a user can conduct a search for a patient's name. The resulting data may be further filtered by any known means, such as by date.

Figure 11:
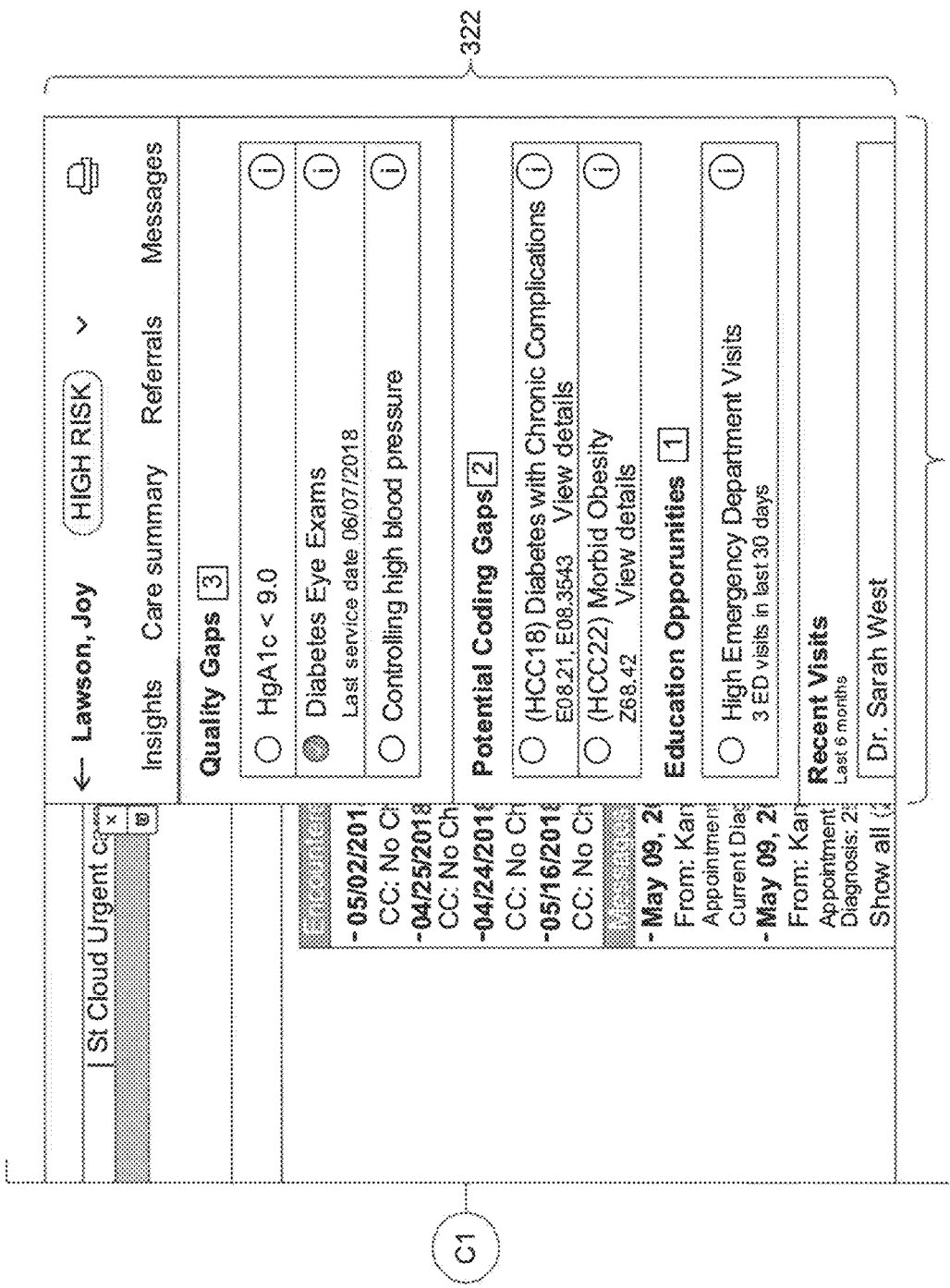
Figure 12:
Figure 12:
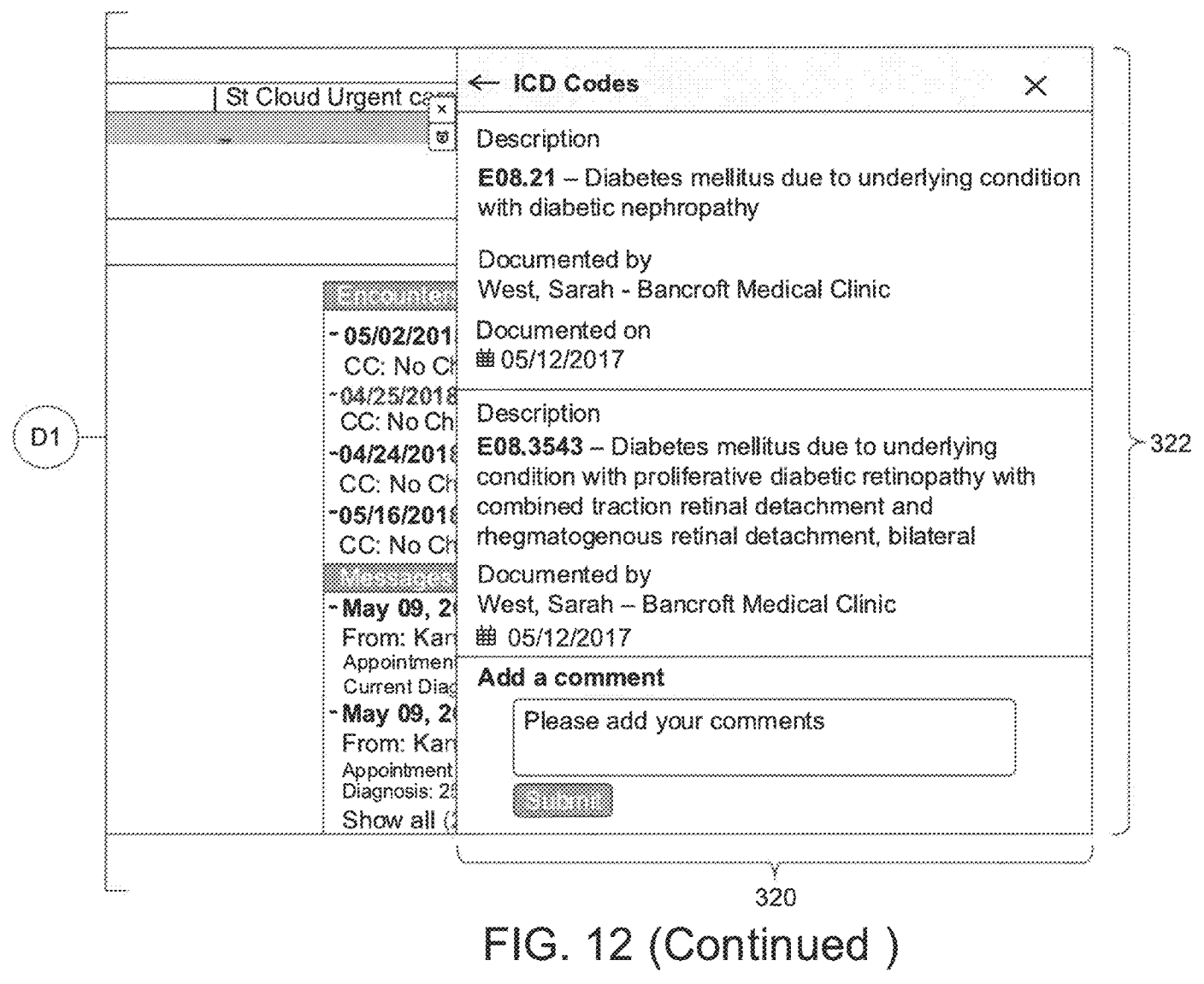

In FIG. 11, the first application 310 displays the panel 320 with the secondary data points 322 for Joy Lawson, the example primary data point 310. Here, the user has selected the secondary data point 322 corresponding with "Diabetes Eye Exam." When the user selects this secondary data point 322, additional information about the diabetes eye exam for Joy Lawson is provided on the panel 320. FIG. 12 provides one example of additional information on a secondary data point 322 which may be shown. Here, the panel 320 displays IDC Codes relating to "diabetes mellitus due to an underlying condition with diabetic nephropathy." As can be seen, the panel 320 provides a vast amount of information to the user, such the name of the documenting individual or organization, the date of documentation, and/or the description of the various codes. The panel 320 also provides a place for the user to add additional information or comments. Additional functionality and features may also be provided by the panel 320, as are recognized by the data illustrated in the figures, as well as other known functionality and features.

As FIGS. 7-12 show, the ability of the user to maintain a view of the first application 310 while simultaneously being able to view the second data points 322, and sub-data points thereof, can vastly improve the usability of the first application 310. The user is not restricted to only viewing information from the first application 310, but rather, be or she can view the related information displayed in the panel 320. This increases the efficiency of the user and ultimately improves productiveness of the user. In turn, this can result in lower medical costs and increased accuracy of medical data analysis.

While various embodiments and examples provided herein are specific to the healthcare and medical fields, the same or similar data structure and functionality described here can be applied to other fields which utilize IT tools and data.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for automatically overlaying computerized visual displays based on contextually related data from multiple applications, the method comprising the steps of:
   automatically capturing, with a computerized device running a first application, a direct, screen-captured, digital image of at least a portion of a graphical user interface (GUI) of the first application visually displayed on a computerized display device of the computerized device;
   identifying at least one primary contextual data point within the captured image, the at least one primary contextual data point being identifying data of a medical patient, wherein the captured image is destroyed after identification of the at least one primary contextual data point;
   searching for a plurality of secondary data points in at least a second application, the second application being a separate and distinct application from the first application, wherein the first and second applications are contextually unrelated whereby there is no communication or sharing of the at least one primary contextual data point between the first and second applications, wherein the plurality of secondary data points are contextually relevant to the primary contextual data point, and wherein the plurality of secondary data points include at least one data point having data about a past historical event associated with the medical patient of the at least one primary contextual data point, the past historical event being retrieved from least one of: a medical record of the medical patient a medical record of a relative of the medical patient or a population-wide medical record;
   fetching at least a portion of the plurality of secondary data points from the second application; and
   visually displaying a panel on the computerized display device of the computerized device concurrently with at least a portion of the GUI of the first application, wherein the panel includes the portion of the plurality of secondary data points.

2. The method of claim 1, wherein capturing the direct, screen-captured, digital image of at least the portion of the GUI of the first application further comprises using a computer vision technique to capture a plurality of direct, screen-captured, digital images over a period of time.

3. The method of claim 2, wherein the computer vision technique captures the plurality of direct screen captured, digital images at predetermined intervals within the period of time.

4. The method of claim 1, wherein identifying the at least one primary contextual data point within the direct, screen-captured, digital image further comprises at least one of: neural network-enabled optical character recognition; pixel comparison and matching; or feature extraction.

5. The method of claim 1, wherein the identifying data of the medical patient of the primary contextual data point further comprises at least one of: a medical provider identity associated with the medical patient; an ID number of the medical patient, a name of the medical patient, or a date of birth of the medical patient.

6. The method of claim 1, wherein at least one of searching for the at least one secondary data point in the second application or fetching the at least one secondary data point from the second application is done without a user logging into the second application.

7. The method of claim 1, wherein visually displaying the panel on the computerized display device concurrently with at least the portion of the GUI of the first application further comprises outsliding the panel from a side of the GUI, whereby the panel displays at least one visual feature and at least one actionable feature.

8. A computer-implemented system for automatically overlaying computerized visual displays based on contextually related data from multiple applications comprising:
   a processor of the computer-implemented system, the processor configured to execute the steps of:
      automatically capture, with the processor of the computer-implemented system running a first application, a direct, screen-captured, digital image of at least a portion of a graphical user interface (GUI) of the first application visually displayed on a computerized display device of the computer-implemented system;
      identify at least one primary contextual data point within the captured image, the at least one primary contextual data point being identifying data of a medical patient, wherein the captured image is destroyed after identification of the at least one primary contextual data point;
      search for a plurality of secondary data points in at least a second application, the second application being a separate and distinct application from the first application, wherein the first and second applications are contextually unrelated whereby there is no communication or sharing of the at least one primary contextual data point between the first and second applications, wherein the plurality of secondary data points are contextually relevant to the primary contextual data point, and wherein the plurality of secondary data points include at least one data point having data about a past historical event associated with the medical patient of the at least one primary contextual data point, the past historical event being retrieved from least one of: a medical record of the medical patient; a medical record of a relative of the medical patient; or a population-wide medical record;
      fetch at least a portion of the plurality of secondary data points from the second application; and visually display a panel on the computerized display device of the computer-implemented system concurrently with at least a portion of the GUI of the first application, wherein the panel includes the portion of the plurality of secondary data points.

9. The computer-implemented system of claim 8, wherein capturing the direct, screen-captured, digital image of at least the portion of the GUI of the first application further comprises using a computer vision technique to capture a plurality of direct, screen-captured, digital images over a period of time.

10. The computer-implemented system of claim 9, wherein the computer vision technique captures the plurality of direct, screen-captured, digital images at predetermined intervals within the period of time.

11. The computer-implemented system of claim 8, wherein identifying the at least one primary contextual data point within the direct screen-captured, digital image further comprises at least one of: neural network-enabled optical character recognition; pixel comparison and matching; or feature extraction.

12. The computer-implemented system of claim 8, wherein the identifying data of the medical patient of the primary contextual data point further comprises at least one of: a medical provider identity associated with the medical patient; an ID number of the medical patient, a name of the medical patient, or a date of birth of the medical patient.

13. The computer-implemented system of claim 8, wherein at least one of searching for the at least one secondary data point in the second application or fetching the at least one secondary data point from the second application is done without a user logging into the second application.

14. The computer-implemented system of claim 8, wherein visually displaying the panel on the computerized display device concurrently with at least the portion of the GUI of the first application further comprises outsliding the panel from a side of the GUI, whereby the panel displays at least one visual feature and at least one actionable feature.

15. A system for automatically overlaying computerized visual displays based on contextually related data from multiple, separate computerized applications, the system comprising:
 a computerized device running a first application and having a graphical user interface (GUI) visually displaying at least a portion of the first application;
 a direct, screen-captured digital image of at least a portion of the GUI of the first application automatically captured with the computerized device running the first application, wherein at least one primary contextual data point within the captured image is identified, the at least one primary contextual data point being identifying data of a medical patient, wherein the captured image is destroyed after identification of the at least one primary contextual data point;
 at least one secondary data point in at least a second application, the second application being separate and distinct from the first application, wherein the first and second applications are contextually unrelated whereby there is no communication or sharing of the at least one primary contextual data point between the first and second applications, wherein the at least one secondary data point is contextually relevant to the primary contextual data point, wherein the at least one secondary data point is fetched from the second application, and wherein the secondary data point includes at least one data point having data about a past historical event associated with the medical patient of the at least one primary contextual data point, the past historical event being retrieved from least one of: a medical record of the medical patient a medical record of a relative of the medical patient or a population-wide medical record; and
 a panel visually displayed on the GUI of the computerized device concurrently with at least a portion of the visually displayed first application, wherein the panel visually displays the at least one secondary data point.

16. The system of claim 15, wherein the at least one primary contextual data point within the captured image is identified using at least one of: neural network-enabled optical character recognition; pixel comparison and matching; or feature extraction.

17. The system of claim 15, wherein the panel visually displayed on the GUI concurrently with at least the portion of the first application further comprises a panel outslid from a side of the GUI, whereby the panel displays at least one visual feature and at least one actionable feature.

18. The system of claim 15, wherein the identifying data of the medical patient of the at least one primary contextual data point further comprises at least one of: a medical provider identity associated with the medical patient; an ID number of the medical patient, a name of the medical patient, or a date of birth of the medical patient.

* * * * *